US00PP18774P2

(12) United States Plant Patent
Chislett

(10) Patent No.: US PP18,774 P2
(45) Date of Patent: Apr. 29, 2008

(54) ORANGE TREE NAMED 'M7'

(50) Latin Name: *Citrus sinensis*
Varietal Denomination: M7

(75) Inventor: Gregory John Kendall Chislett, Kenley VIA Piangil (AU)

(73) Assignee: Chislett Investments Pty Ltd, Kenley, Victoria (AU)

( * ) Notice: Subject to any disclaimer, the term of this patent is extended or adjusted under 35 U.S.C. 154(b) by 0 days.

(21) Appl. No.: 11/497,942

(22) Filed: Aug. 1, 2006

(51) Int. Cl.
*A01H 5/00* (2006.01)

(52) U.S. Cl. ..... Plt./202

(58) Field of Classification Search ..... Plt./202, Plt./201
See application file for complete search history.

(56) References Cited

U.S. PATENT DOCUMENTS

PP11,246 P * 2/2000 Weigall ..... Plt./202

* cited by examiner

*Primary Examiner*—Kent Bell
*Assistant Examiner*—S. B. McCormick-Ewoldt
(74) *Attorney, Agent, or Firm*—Stratton Ballew PLLC

(57) ABSTRACT

A new orange tree (*Citrus sinensis*) named 'M7' is disclosed. 'M7' is a limb sport mutation of 'Navelina 7.5'. 'M7' is notable for its high quality, uniformly globose fruit, which colors and matures very early as compared to its parent and to other known varieties.

5 Drawing Sheets

Latin name of the genus and species of the plant claimed: *Citrus sinensis.*
Variety denomination: 'M7'.

BRIEF DESCRIPTION OF THE VARIETY

'M7' was first discovered as a limb sport mutation of 'Navelina 7.5' (not patented) in a cultivated commercial orchard near Kenley, Victoria, Australia in May 2004. The inventor observed that fruit on one branch of the parent tree colored approximately 3 weeks earlier than other fruit on the tree. Further testing confirmed that the internal maturity of the fruit was equally advanced. Budwood from the sport limb was grafted onto 'Citrange' (not patented) and 'Volkameriana' (not patented) rootstocks in October 2004 at Kenley. The traits first observed in the limb sport mutation 'M7' have been carried forward and remain stable and true to type in the asexually propagated trees of 'M7'.

'M7' has been compared to its parent 'Navelina 7.5' and to other known cultivars, and has been found to exhibit several characteristics which distinguish it and are commercially desireable. A comparison of 'M7' and 'Navelina 7.5' is provided in Table 1, below:

TABLE 1

| Characteristic | 'M7' | 'Navelina 7.5 ' |
|---|---|---|
| Fruit shape | Rounded | Elongated |
| Colouring | Early colouring | Later colouring |
| Leaf shape | Rounded | Elongated |
| Leaf surface | Blistered | Smoother |
| Brix | Higher | Lower |

As noted above, the new variety colors and matures a full 3 weeks before 'Navelina 7.5'. The inventor is not aware of any commercially available navel orange cultivar that matures earlier than 'M7.' The fruit of 'M7' are further distinguishable by their more uniform globose shape, as compared to 'Navelina 7.5'. Leaves of 'M7' tend to be broader than those of 'Navelina 7.5'.

BRIEF DESCRIPTION OF THE PHOTOGRAPHS

DETAILED BOTANICAL DESCRIPTION OF THE VARIETY

Figure 1:
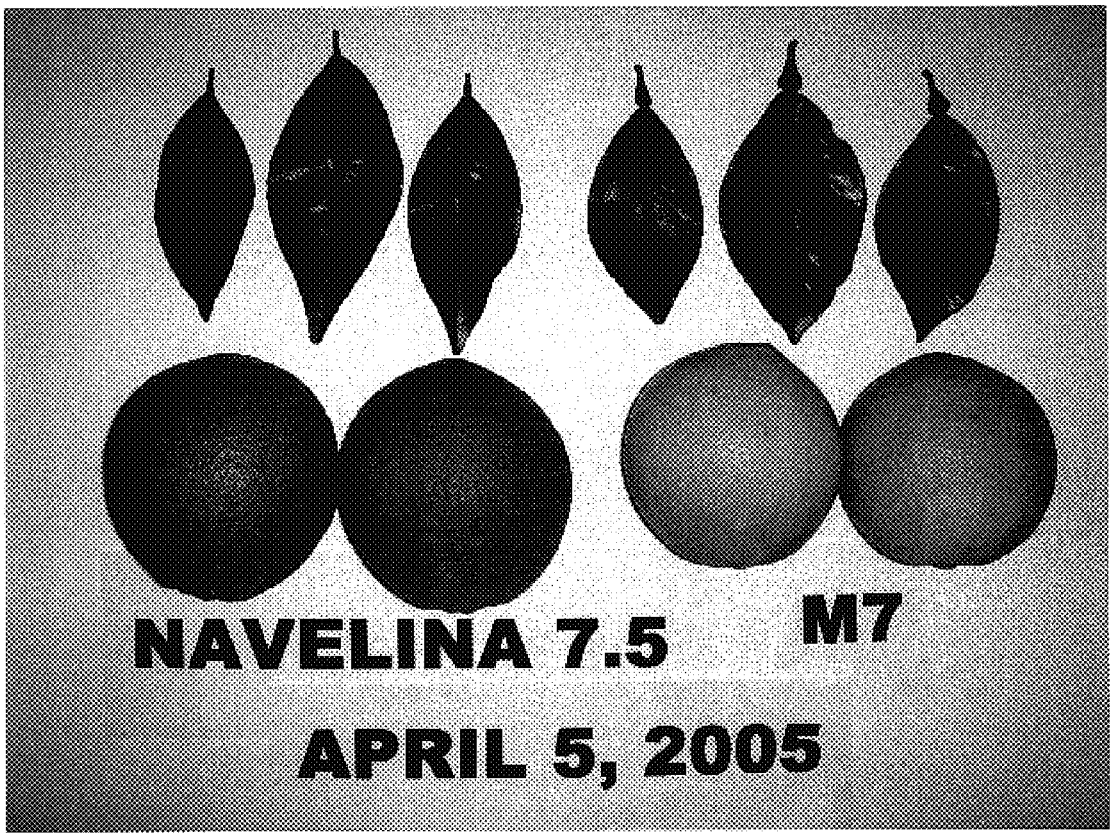
FIG. 1 shows fruit and leaves of 'M7' as compared to parent cultivar 'Navelina 7.5' Apr. 5, 2005, Kenley, Victoria, Australia)
Figure 2:
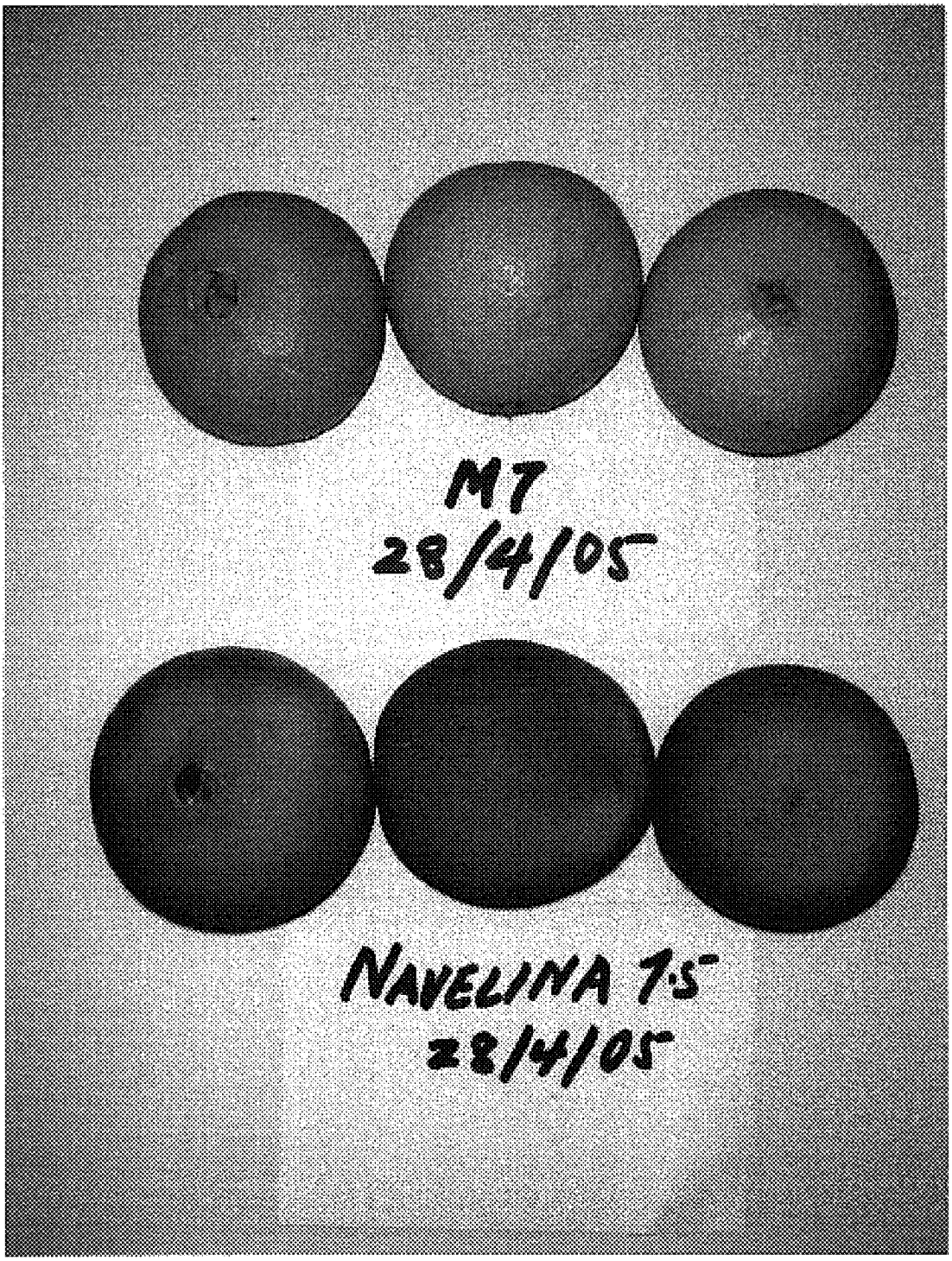
FIG. 2 shows fruit of 'M7' as compared to parent cultivar 'Navelina 7.5' (Apr. 28, 2005, Kenley, Victoria, Australia)
Figure 3:
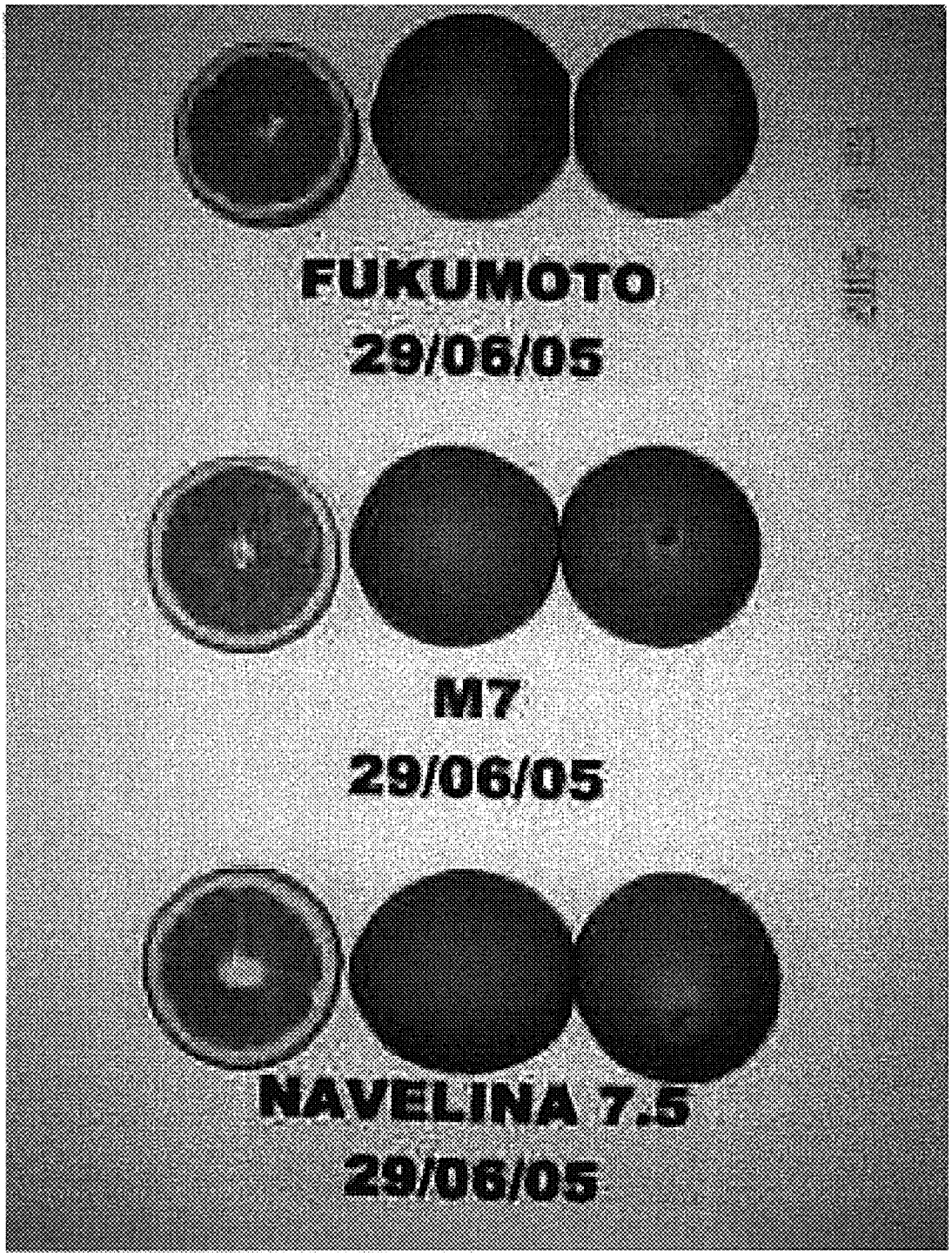
FIG. 3 shows whole and sectioned fruit of 'M7' as compared to 'Fukumoto' and 'Navelina 7.5' Jun. 29, 2005, Kenley, Victoria, Australia)
Figure 4:
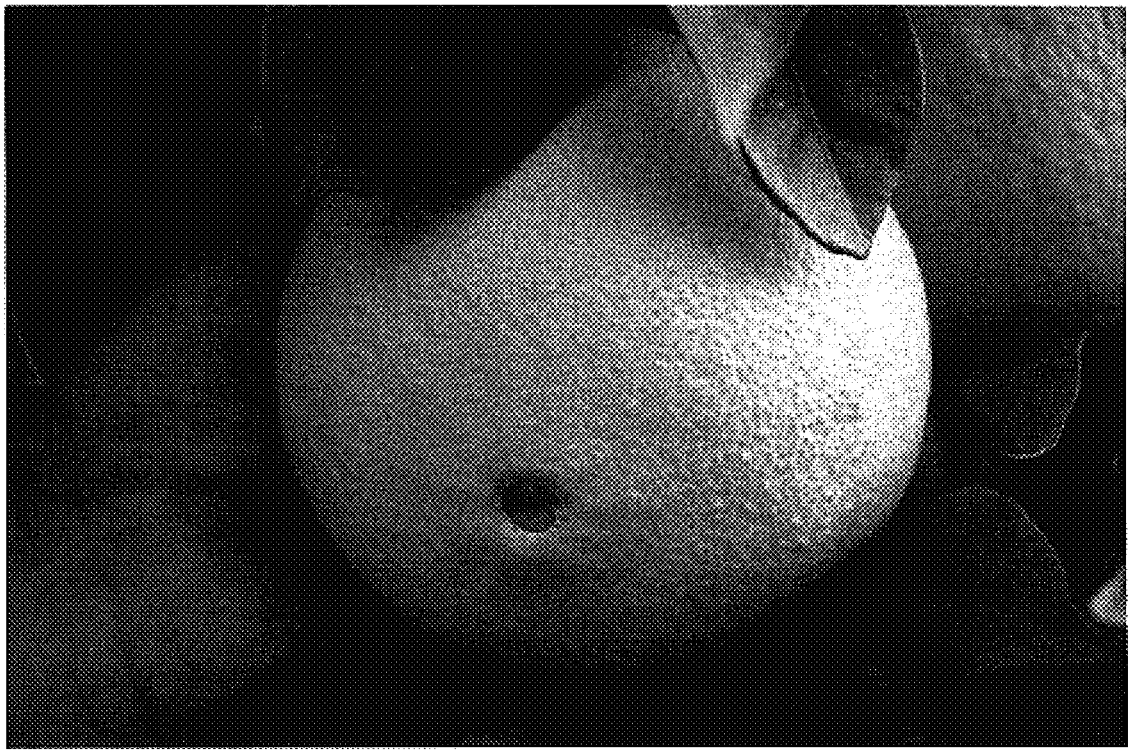
FIG. 4 shows fruit and leaves of 'M7'.
Figure 5:
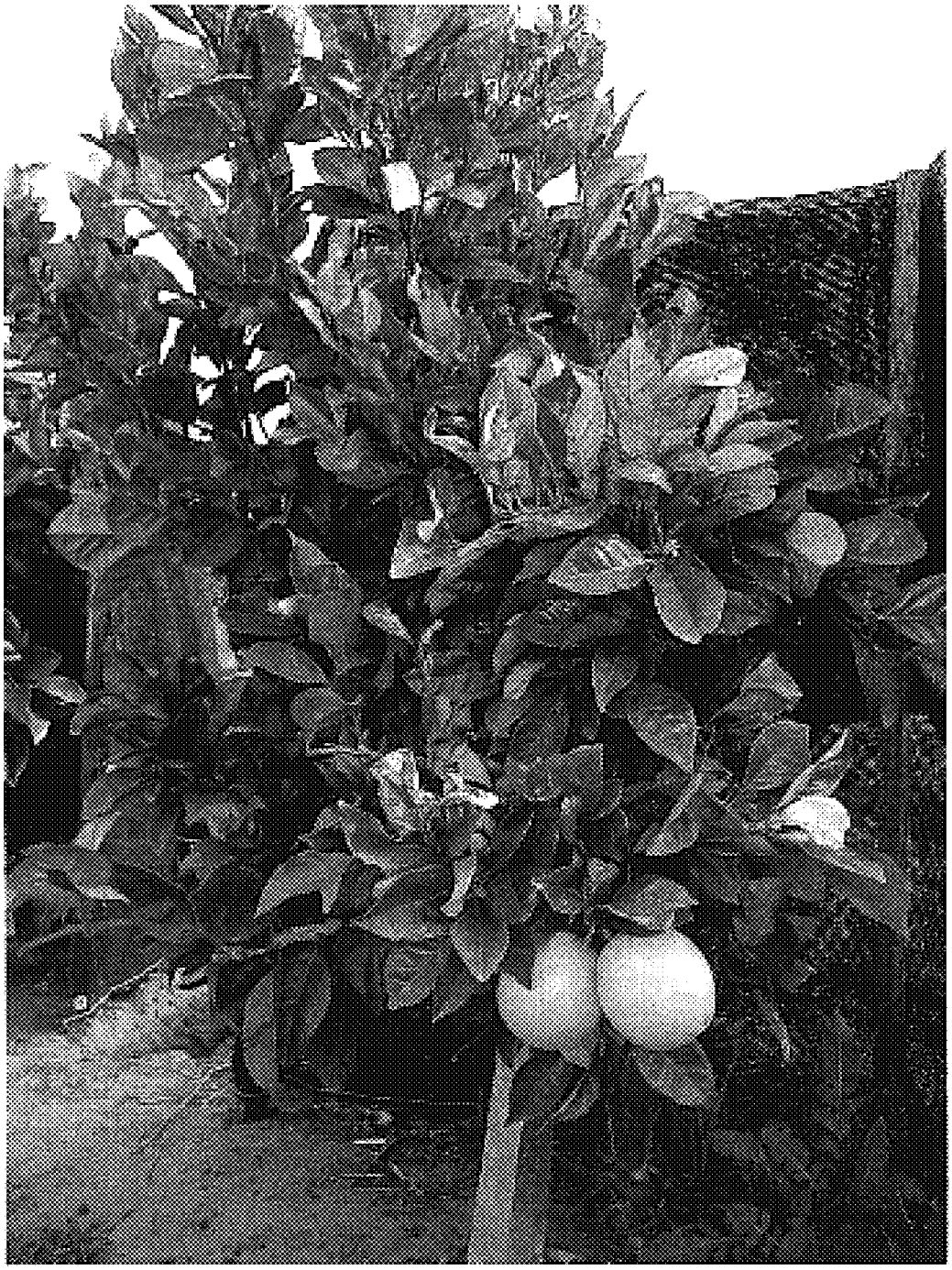
FIG. 5 shows a 2 year old tree of 'M7'.

The following is a detailed botanical description of the new orange tree 'M7', based on observations made during the 2006 and 2007 growing seasons at Kenley, Victoria, Australia, of trees planted in 2005 on 'Citrange' and 'Volkameriana' rootstock. Colors are described with reference to The Royal Horticultural Society Colour Chart. It should be understood that the botanical and analytical characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree: More vigorous than 'Navelina 7.5'; canopy open, less dense than 'Navelina 7.5'; Size—height 1.4 to 1.7 m, spread 0.8 to 1.5 m; Growth habit upright to spreading;

Trunk—diameter 3.1 cm at 30 cm above ground, bark color greyed orange 164B, greyed purple N187D, greyed yellow 161C, texture smooth to medium; Tendency toward alternate bearing—low; Winter hardiness, chilling requirement, and drought tolerance—similar to 'Navelina 7.5'.

Branch: Size—length 51 cm, diameter 1.75 cm; Crotch angle 15° to 45°; Bark—color green 137A with orange white 159A, texture similar to 'Navelina 7.5'.; Thorns—absent or sparse, short, length 3 mm, occasionally up to 20 mm on some trees; Current year shoot—length 54 cm, color green 137A.

Flowers: Buds—oval (just prior to anthesis), length 11 to 13 mm, diameter 7 mm; color white 155A; Blossoms—2 to 5 per cluster, margins not touching; Size—diameter 37 mm when fully opened, depth 16.5 mm; Pollen—scant, presumed sterile.

Sepals: Size—length 4 to 5 mm, width 4 mm; Shape—acute angled triangle, with rare or no emargination of apex, margin smooth; Color—upper surface yellow green 145B; lower surface yellow green 145A.

Petals: Quantity—5 per flower; Shape—elliptical with acute tip, margin smooth; Size—length 18.5 mm, width 8.5 mm; Color—upper surface white 155B, lower surface white 155D with translucent flecks of green 145B.

Bloom:

| Event | 2006 | 2007 |
|---|---|---|
| Date of first bloom (first flower open) | Sep. 29 | Sep. 23 |
| Date of full bloom | Oct. 6 | Oct. 3 |
| Date of first fruitlet fall | Oct. 16 | Oct. 12 |

Pedicel: Size—length 8 mm, diameter 1.5 to 2 mm; color yellow green 145A.

Reproductive organs: Pistil—one per flower, 6 to 12 mm long, color yellow green 145D; Anthers—20 per flower, length 10 mm (including filament), color greyed yellow 161A; Stigma—1 per flower, length 1 to 3 mm, color greyed yellow 162C; Style—1 per flower, length 2 to 6 mm; color yellow green 145C; Ovary—1 per flower, length 2 to 3 mm, width 2 to 3 mm, color yellow green 144B.

Leaves: Size—length 96 mm, width 61 mm, ratio of length to width 1.6:1; Shape—elliptic to lanceolate with acute base and apex, pronounced raised veins and mild blistering, little or no crenation of the margin; Color—upper surface green 137C, green 141B, yellow green 147A, lower surface green 137C; Petiole—length 22.6 mm, longer than 'Navelina 7.5', wings pronounced, wing width 10.6 mm, color green 137C, green 141B, yellow green 147A.

Fruit: 5 per cluster; Shape—globose; Size—axial diameter 89 mm, apical diameter 87.6 mm, weight 350 g; Navel—present; Rind color—yellow orange 23A; Oil glands—68 per $cm^2$, diameter 1 to 2 mm; Rind thickness—1.5 to 3.5 mm; Ease of peeling—not easy to peel, similar to 'Navelina 7.5'; Rind texture—medium, slightly smoother than 'Navelina 7.5'; Albedo—color yellow 11C; Fruit segments—quantity 10 per fruit; Toughness of segment membrane—moderate to weak membrane to weak membrane, similar to 'Navelina 7.5'; Juice sac—length 14 mm, elongated, length to width ratio 6:1, color yellow orange 21A; Juice—soluble solids (°Brix) in 'M7' fruit consistently higher than °Brix in 'Navelina 7.5' fruit, with 'M7' achieving 10°Brix four weeks wearlier than 'Navelina 7.5' in 2007 and more than eight weeks earlier in 2006 (see Tables 2 and 3); Harvest maturity—3 weeks before 'Navelina 7.5', harvest window early April to mid- to late July in Kenley, Victoria, Australia.

TABLE 2

2005 Comparative Analysis of 'M7' and 'Navelina 7.5'

| Date | Variety | Juice % | Brix | Acid % | Ratio |
|---|---|---|---|---|---|
| Apr. 5, 2005 | M7 | 36 | 11.6 | 1.38 | 8.4 |
| Apr. 5, 2005 | Navelina 7.5 (Spain) | 34 | 9.7 | 1.38 | 7.0 |
| Apr. 28, 2005 | M7 | 41 | 12.7 | 1.16 | 10.9 |
| Apr. 28, 2005 | Navelina 7.5 (Spain) | 43 | 10.1 | 1.02 | 9.9 |
| Jun. 7, 2005 | M7 | 47 | 13.2 | 1.08 | 12.2 |
| Jun. 7, 2005 | Navelina 7.5 (Spain) | 49 | 10.8 | 1.02 | 10.6 |
| Jun. 30, 2005 | M7 | 55 | 13.1 | 0.87 | 15.1 |
| Jun. 30, 2005 | Navelina 7.5 (Spain) | 54 | 10.9 | 0.92 | 11.8 |

TABLE 3

Comparison of °Brix in 'M7' and 'Navelina 7.5 ' (2005-2007)

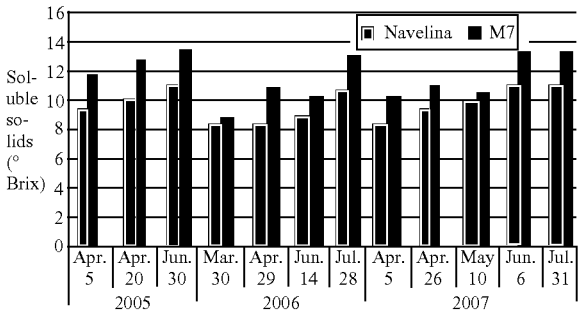

Seeds: Fruit of 'M7' do not produce seeds.

Stem: Length 9.4 mm, diameter 5.3 mm; color green 137A with orange white 159A stations.

Market use: Fresh market.

Maturity and harvest dates: 'M7' fruit reach market-preferred specifications for juice content, soluble solids and acid by early April, making it an early navel variety. Recommended values are reached in M7 fruit approximately 2 weeks earlier than in 'Navelina 7.5' fruit. Fruit is suitable for harvesting 10 to 14 weeks from first maturity, depending on seasonal conditions.

It is claimed:

1. A new and distinct orange tree, substantially as described and illustrated herein.

* * * * *